(12) United States Patent
Agrama

(10) Patent No.: US 7,141,713 B2
(45) Date of Patent: Nov. 28, 2006

(54) METHOD FOR REDUCING PRESSURE DAMAGE TO SKIN OF A PERSON, AND CORRESPONDING SKIN PROTECTIVE DEVICES

(76) Inventor: Hani M. Agrama, 255 Andros Ave., Cocoa Beach, FL (US) 32931

(*) Notice: Subject to any disclaimer, the term of this patent is extended or adjusted under 35 U.S.C. 154(b) by 308 days.

(21) Appl. No.: 10/615,963

(22) Filed: Jul. 9, 2003

(65) Prior Publication Data
US 2005/0005944 A1    Jan. 13, 2005

(51) Int. Cl.
*A61F 13/00* (2006.01)
*A61F 5/30* (2006.01)

(52) U.S. Cl. ............... 602/43; 602/41; 602/42; 602/57; 602/58; 128/118.1; 128/117.1; 128/888; 128/889

(58) Field of Classification Search .......... 602/41, 602/42, 43, 52, 57, 58; 128/888, 889
See application file for complete search history.

(56) References Cited

U.S. PATENT DOCUMENTS

| | | | |
|---|---|---|---|
| 1,382,831 A | 6/1921 | Hilker | |
| 4,266,298 A | 5/1981 | Graziano | 2/22 |
| 4,436,089 A | 3/1984 | Schmid | 128/155 |
| 4,614,000 A | 9/1986 | Mayer | 5/484 |
| 4,669,460 A | 6/1987 | Silber | 128/149 |
| 4,952,618 A * | 8/1990 | Olsen | 524/17 |
| 4,962,769 A | 10/1990 | Garcia | 128/889 |
| 5,170,781 A * | 12/1992 | Loomis | 128/118.1 |
| 5,364,339 A | 11/1994 | Carver | 602/47 |
| 5,462,519 A | 10/1995 | Carver | 602/47 |
| 5,882,324 A | 3/1999 | Baranowski | 602/65 |
| 5,944,683 A | 8/1999 | Baranowski | 602/65 |
| 6,096,943 A * | 8/2000 | Maiwald | 602/48 |
| 2002/0032485 A1 | 3/2002 | Flam et al. | 623/23.51 |

\* cited by examiner

*Primary Examiner*—Henry Bennett
*Assistant Examiner*—Annette Dixon
(74) *Attorney, Agent, or Firm*—Allen, Dyer, Doppelt, Milbrath & Gilchrist, P.A.

(57) ABSTRACT

A method for reducing pressure damage to skin of a person includes determining a location on the person susceptible to pressure damage, and adhesively securing a skin protective device to the location. The skin protective device includes a substrate having an inner surface, and an outer surface. An adhesive layer substantially covers the inner surface, and at least one fluid-filled cell is on the outer surface to cushion the skin of the person.

36 Claims, 4 Drawing Sheets

METHOD FOR REDUCING PRESSURE DAMAGE TO SKIN OF A PERSON, AND CORRESPONDING SKIN PROTECTIVE DEVICES

FIELD OF THE INVENTION

The present invention relates to the field of health care, and in particular, to a method and corresponding skin protective devices for reducing pressure damage to skin of a person, particularly for a bedridden person.

BACKGROUND OF THE INVENTION

Decubitus ulcers, also known as pressure sores, are difficult to treat medical problems that can lead to serious consequences. Pressure sores occur when the skin breaks down as a result of continuous pressure, thus forming open sores. Pressure sores frequently affect the skin over bony prominences of the body. Areas most commonly affected include the skin over the heel, ankle bones, coccyx or tailbone, trochanters or hip bones and the sacral area of the lower back.

An estimated 2 to 3 million people in the United States are affected by pressure sores, with most of them being elderly. One study showed that over 12% of nursing home residents developed pressure sores within their first year. This number increases to 20% after 2 years. Moreover, an estimated 60,000 people die from pressure sore complications every year.

Pressure sores occur when there is a lack of blood supply to a dependent area of the body. This lack of blood supply is caused by compression of the skin and underlying soft tissue between the bony prominence and a supporting surface, such as a mattress. The weight of the body part exerts sufficient pressure to impair the blood supply to the soft tissue and skin. If this impairment of the blood supply is prolonged, permanent injury results causing necrosis or death of the skin and underlying soft tissue in the affected area. Other factors causing pressure sores include friction of the skin against bed sheets, casts or braces.

Pressure sores commonly affect individuals with limited mobility, such as those confined to a bed because of illness, injury or old age. These are frequent problems in nursing home patients, especially those with circulatory problems, or impaired sensations because of diabetes or stroke.

Once a pressure sore occurs, treatment is very difficult and time consuming, often requiring weeks or months of wound care. Dressing changes are usually painful to the patient. Complications, including localized or generalized infection, may be serious and commonly require hospitalization for proper treatment. Surgical intervention is frequently required, including debridement or excision of dead tissue, skin grafting and even leg amputation.

Pressure sores are generally considered to be a preventable condition, but prevention has proven to be difficult, time consuming and costly. Prevention requires avoiding prolonged pressure on any area of the skin by frequently moving the patient, and attention to skin care is required to avoid irritation or chaffing.

Published patent application no. 2003/0032485 to Flam et al. discloses a number of skin protective devices for preventing pressure sores. In particular, the skin protective devices have an inner surface which conforms to the body part to be protected, and is made of a material suitable for distributing the weight of the body part over an extended area.

A bed pad comprising a plurality of air-filled cells for treating pressure sores is disclosed in U.S. Pat. No. 5,462,519 to Carver. A skin protective device for ankles, heels and elbows is disclosed in U.S. Pat. No. 5,944,683 to Baranowski. In Baranowski, the skin protective device is a cushion formed of a closed cell foam having a resilience with respect to pressure. The resilient cushioning foam may include air, gel or water.

Other skin protective devices such as air mattresses and floatation beds, foam, silicon gel, sponge rubber and sheepskin pads of various shapes have been available—but these are difficult to apply or maintain in position. Moreover, some are uncomfortable to the patient and some are prohibitively expensive.

In spite of these efforts, the incidence of pressure sores has not diminished. In fact, the problem is becoming more frequent as the population ages. More individuals require long-term care and are confined to nursing homes. As nursing homes become more short-staffed, caregivers have even less time to devote to frequently changing a patient's position, and to providing attention to skin care. There exists a need for a straightforward skin protective device that can be easily applied to a vulnerable area of the body, stays in position once applied, and does not cause discomfort.

SUMMARY OF THE INVENTION

In view of the foregoing background, an object of the present invention is to reduce pressure damage to the skin of a person using a skin protective device that overcomes the above noted limitations.

This and other objects, advantages and features in accordance with the present invention are provided by a method comprising determining at least one location on the person susceptible to pressure damage, and adhesively securing a skin protective device to the at least one location. The skin protective device may comprise a substrate having an inner surface and an outer surface, an adhesive layer substantially covering the inner surface, and at least one fluid-filled cell on the outer surface. The fluid-filled cell advantageously increases the area over which the pressure is distributed, thereby reducing the effects of the pressure.

The adhesive layer may cover at least 75% of the inner surface of the substrate for adhesively securing the skin protective device to the skin of the person. The skin protective device is easily applied to the skin and is held in position via the adhesive layer without causing unnecessary discomfort to the person. The skin protective device may further comprise a removable protective layer on the adhesive layer, and the method may further comprise removing the protective layer before adhesively securing the skin protective device.

The at least one fluid-filled cell may comprise a single fluid-filled cell, or a plurality of fluid-filled cells in a side-by-side relation. Each fluid-filled cell may also define an exposed outermost surface for the skin protective device. The fluid-filled cell may be filled with a gas, such as air, or a liquid or a gel.

The substrate may have a substantially uniform thickness throughout. In one embodiment, the substrate comprises a polymer, and the adhesive layer comprises hydrocolloid. The substrate may have either a flat shape or a predetermined arcuate shape. Also, the substrate may comprise a flexible material or a shape-retaining material.

DETAILED DESCRIPTION OF THE PREFERRED EMBODIMENTS

The present invention will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout, and prime and multiple prime notations are used to indicate similar elements in alternate embodiments.

Figure 1A:
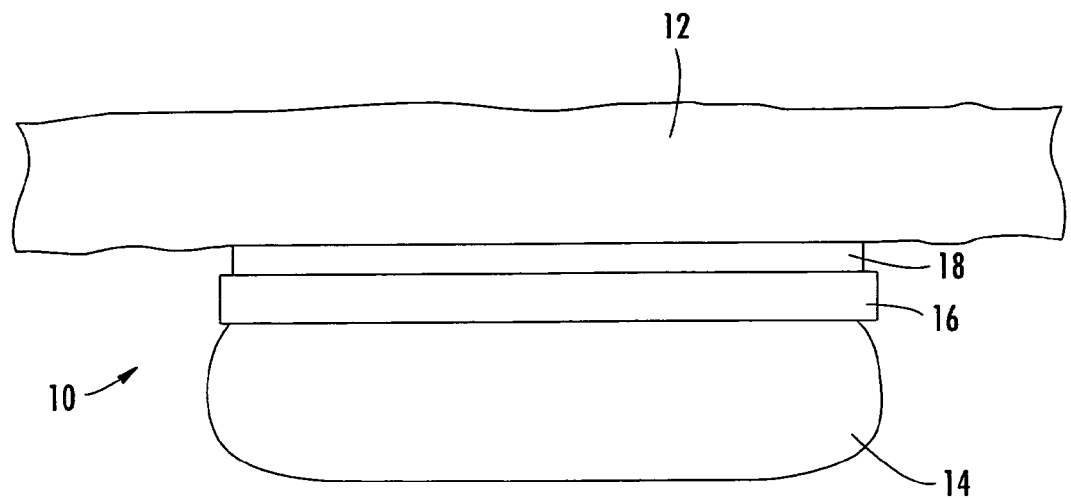
FIG. 1a is a side view of a skin protective device applied to the skin of a person in accordance with the present invention.

A method for reducing pressure damage to the skin of a person in accordance with the present invention is based upon application of any of the various embodiments of a skin protective device illustrated in FIGS. 1a–4. The method initially comprises determining at least one location 12 on the person susceptible to pressure damage, and adhesively securing a skin protective device 10 to that location, as illustrated in FIG. 1a.

A bedridden person, for example, has several locations on their body that are susceptible to skin irritations. These locations generally include an underlying bone structure having a bony prominence that concentrates the weight of the person over a small region that increases the pressure at an interface between the bony prominence and the corresponding skin and soft tissue. The skin protective device 10 includes at least one fluid-filled cell 14 that advantageously increases the area over which the pressure is distributed, thereby reducing the effects of the pressure.

Figure 1B:
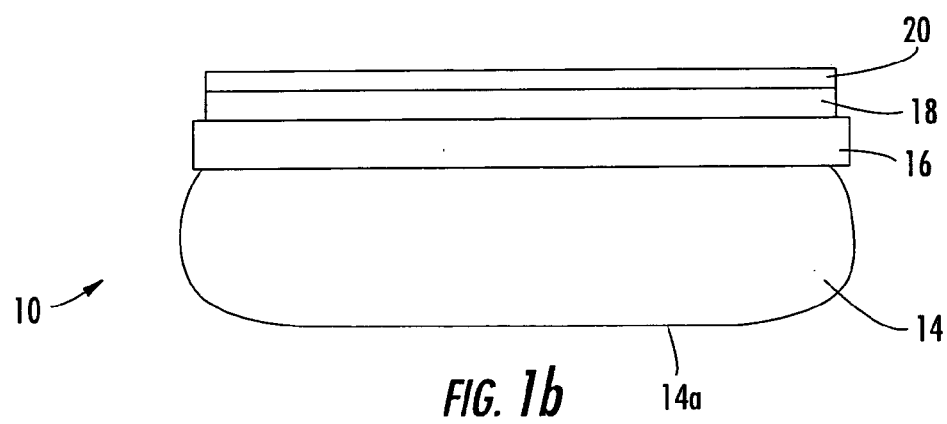
FIG. 1b is a side view of the skin protective device illustrated in FIG. 1a before being applied to the skin of the person.

Referring now to FIG. 1b, the skin protective device 10 in accordance with the present invention will be discussed in greater detail. The illustrated skin protective device 10 includes a substrate 16 having an inner surface to be positioned adjacent the skin 12 of the person. An adhesive layer 18 substantially covers the inner surface of the substrate 16 for adhesively securing the skin protective device 10 to the skin 12. The skin protective device 10 is easily applied to the skin 12, and is held in position via the adhesive layer 18 without causing discomfort to the person. A removable layer 20 protects the adhesive layer 18 prior to application to the skin 12.

The adhesive layer 18 covers at least 75% of the inner surface of the substrate 16 so that it can advantageously hold the skin protective device 10 in position. The adhesive layer 18 may be similar to medical grade tape, for example. Moreover, the adhesive layer 16 may comprise a medicated dressing, such as a hydrocolloid or a hydrogel material.

The adhesive layer 18 is not limited to any particular pattern on the inner surface of the substrate 16. For example, the adhesive layer 18 may be formed as a solid or contiguous pattern, as readily appreciated by those skilled in the art. Alternately, the adhesive layer 18 may be in the form of spaced apart strips or even intersecting strips. Other patterns are readily acceptable as long as the adhesive layer 18 covers at least 75% of the inner surface of the substrate 16.

Figure 1C:
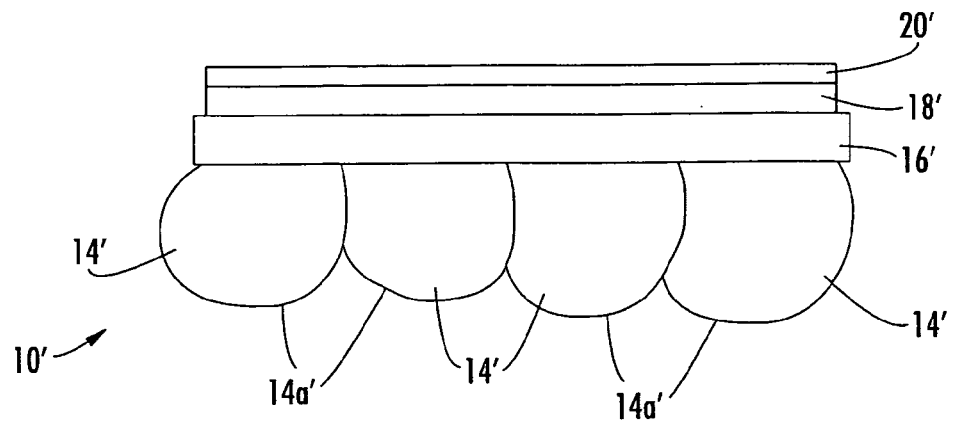
FIG. 1c is a side view of another embodiment of the skin protective device in accordance with the present invention.

At least one fluid-filled cell 14 is on an outer surface of the substrate 16 to cushion the skin 12. The fluid-filled cell 14 may be a single cell as illustrated in FIGS. 1a and 1b, or a plurality of cells 14' in a side-by-side relation as illustrated in FIG. 1c. The fluid-filled cells 14, 14' respectively define an exposed outermost surface 14a, 14a' for the skin protective device 10, 10'. The exposed outermost surfaces 14a, 14a' of the fluid-filled cells 14, 14' contact the support surface resulting in pressure being applied to the skin 12.

The fluid-filled cells 14a, 14a' are filled with either a gas or a liquid, as readily appreciated by those skilled in the art. The gas preferably includes air, whereas the liquid includes a water or saline-based solution, for example. The fluid-filled cells 14a, 14a' may also be filled with a gel, as readily appreciated by those skilled in the art. The fluid-filled cells 14a, 14a' are preferably formed using a light-weight plastic material bonded to the substrate 16, 16'. Of course, other types of materials suitable for retaining the gas or liquid may be used, as readily appreciated by those skilled in the art.

The fluid-filled cells 14a, 14a' are strong enough to withstand the pressure applied to it by the weight of the part of the body to which the skin protective device 10, 10' is applied. The pressure in each of the fluid-filled cells 14a, 14a' is low enough to allow each cell to be deformable by the weight of the body part, but high enough to prevent the body part from contacting the support surface. The size/volume of each fluid-filled cell 14a, 14a' depends on the size of the skin protective device 10, 10'. Larger skin protective devices 10, 10' have proportionally larger fluid-filled cells 14a, 14a'.

Figure 2A:
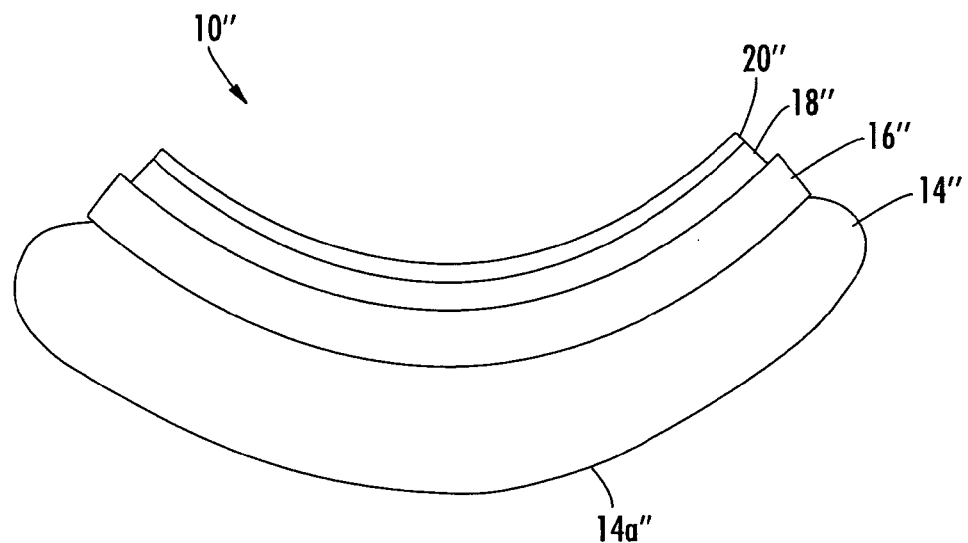
FIG. 2a is a side view of another embodiment of the skin protective device similar to that illustrated in FIGS. 1a and 1b but with a predetermined arcuate shape.
Figure 2B:
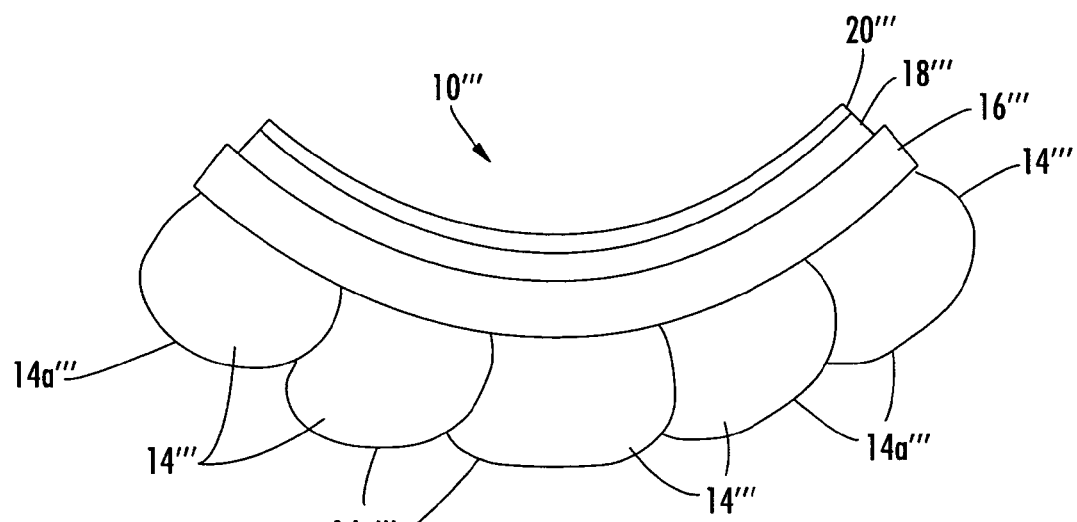
FIG. 2b is a side view of another embodiment of the skin protective device similar to that illustrated in FIG. 1c but with a predetermined arcuate shape.

The illustrated substrate 16, 16' preferably has a uniform thickness, and is preferably made out of polymer, for example, or another compatible type material, as readily appreciated by those skilled in the art. The substrate 16, 16' may also be formed with a non-uniform thickness. In one embodiment, the substrate 16, 16' has a flat shape as illustrated in FIGS. 1a–1c. The flat shape is preferably suited for the flat surfaces of the body. In another embodiment, the substrate 16", 16'" has a predetermined arcuate shape as illustrated in FIGS. 2a and 2b. The predetermined arcuate shape allows the skin protective device 10", 10'" to conform to the parts of the body having a bony prominence.

The illustrated skin protective devices 10, 10', 10" and 10'" in accordance with the present invention can be made in different shapes and sizes to fit different parts of the body. The different parts of the body in which the skin protective devices 10, 10', 10" and 10'" can be applied include, for example, the toe, heel, ankle, trochanter, knee, sacrum, coccyx, buttocks, ischium, scapula, elbow and occiput.

Figure 4:
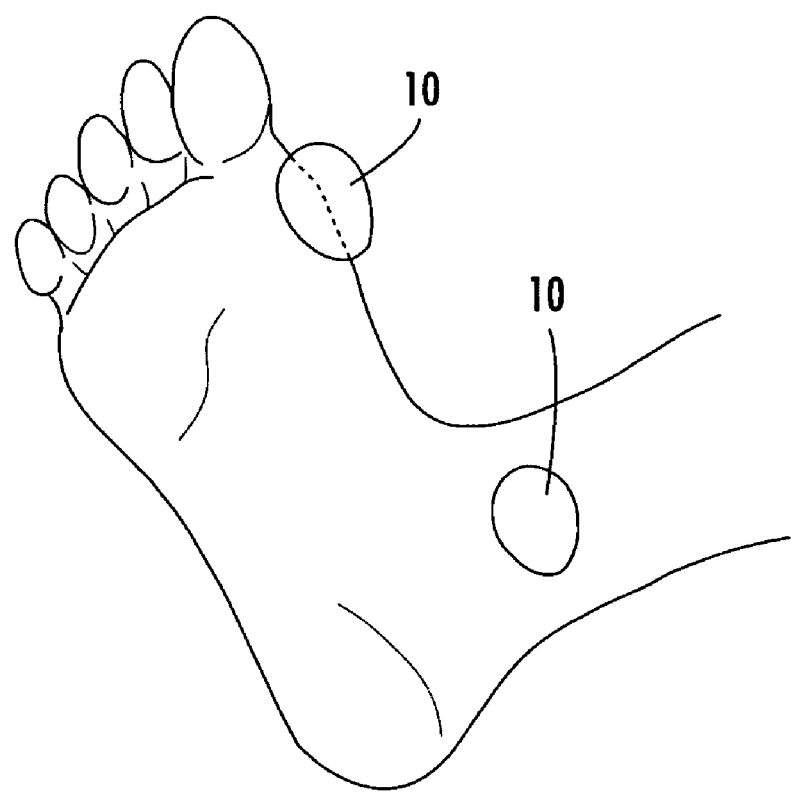
FIG. 4 is a side view of a person's foot with skin protective devices in accordance with the present invention applied to different locations susceptible to pressure damage.

Depending on the intended application, the substrate 16, 16', 16" and 16''' may comprise a flexible material or a shape-retaining material. A small skin protective device with a flexible substrate may be applied to the foot to prevent pressure sores from shoes, for example, as illustrated in FIG. 4. The size of such a skin protective device 10 would be small enough to fit within the shoe when worn by the person. The fluid-filled cell 14 in this application is preferably a single cell.

Figure 3A:
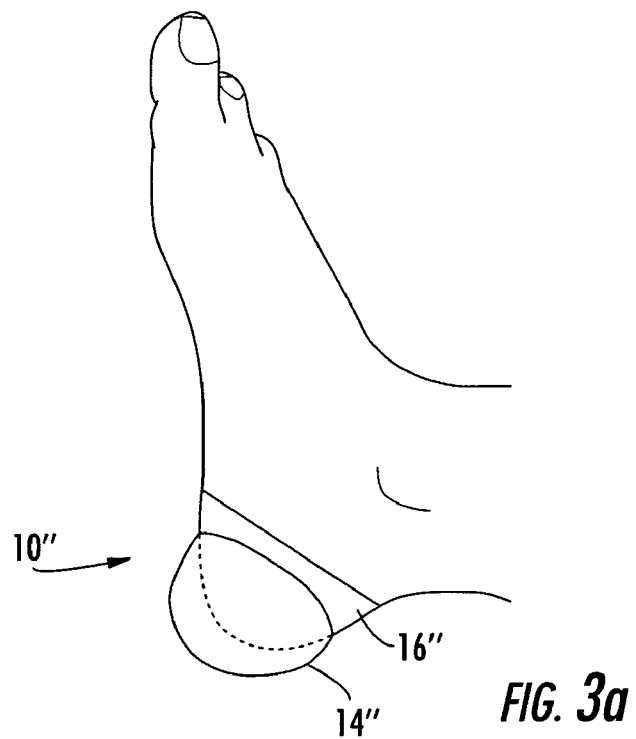
FIG. 3a is a side view of a person's foot having yet another embodiment of a skin protective device with a single fluid-filled cell in accordance with the present invention applied to the heel.
Figure 3B:
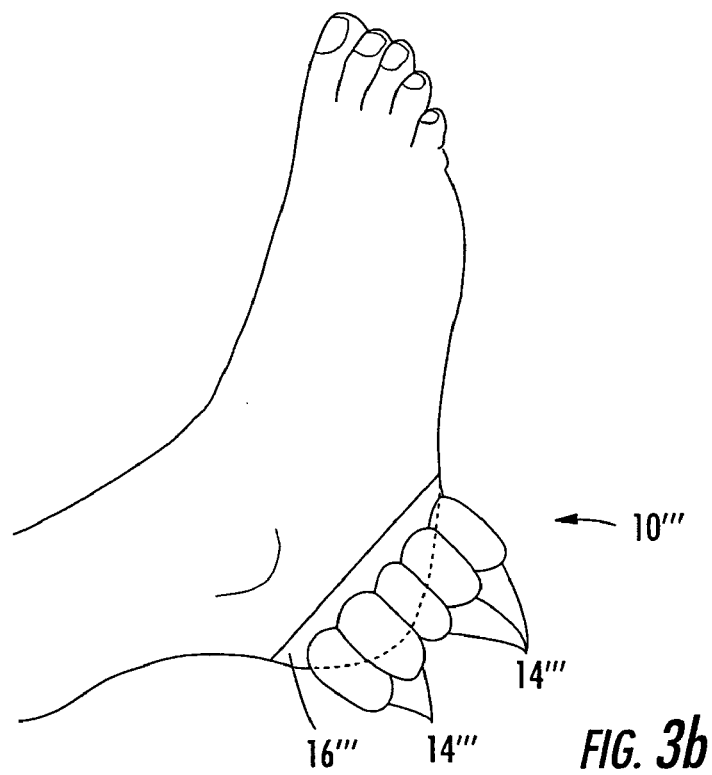
FIG. 3b is a side view of a person's foot having still another embodiment of a skin protective device with a plurality of fluid-filled cells in accordance with the present invention applied to the heel.

Larger skin protective devices are preferred for the larger, flat surfaces of the body. Bony prominence areas such as the ankle, heel and elbow are preferably protected by a skin protective device 10", 10''' with a shape-retaining material, as best illustrated in FIGS. 3a and 3b. The illustrated shape is in the form of a cup to fit the body part, such as the heel.

Another aspect of the present invention is directed to a skin protective device in which the adhesive layer is applied directly to a fluid-filled cell as readily appreciated by those skilled in he art. In other words, the skin protective device does not include a substrate, or alternatively, the substrate is integrated with the adhesive layer. In particular, the skin protective device comprises an adhesive layer having an inner surface to be adhesively secured to the skin of the person, and an outer surface. At least one fluid-filled cell has an outer surface to cushion the skin of the person, and an inner surface. The outer surface of the adhesive layer substantially covers the inner surface of the at least one fluid-filled cell. A removable layer may be on the inner surface of the adhesive layer for protection thereof prior to application to the skin of the person.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A method for reducing pressure damage to skin of a person, the method comprising:
   determining at least one location on the person susceptible to pressure damage; and
   adhesively securing a skin protective device to the at least one location, the skin protective device consisting of a substrate having an inner surface and an outer surface opposite the inner surface, an adhesive layer substantially covering the inner surface for adhesively securing the substrate to the skin of the person, and at least one fluid-filled cell on the outer surface of the substrate and positioned overlying the adhesive layer so that the substrate distributes pressure when applied to the skin of the person, the at least one fluid-filled cell retaining the fluid therein to cushion the skin of the person.

2. A method according to claim 1 wherein the skin protective device further comprises a removable protective layer on the adhesive layer; and further comprising removing the protective layer before adhesively securing the skin protective device.

3. A method according to claim 1 wherein the at least one fluid-filled cell comprises a plurality of fluid-filled cells in a side-by-side relation.

4. A method according to claim 1 wherein the at least one fluid-filled cell defines an exposed outermost surface for the skin protective device.

5. A method according to claim 1 wherein the at least one fluid-filled cell is filled with at least one of a gas, liquid and gel.

6. A method according to claim 1 wherein the adhesive layer covers at least 75% of the inner surface of the substrate.

7. A method according to claim 1 wherein the substrate has a substantially uniform thickness throughout.

8. A method according to claim 1 wherein the substrate comprises a polymer; and wherein the adhesive layer comprises hydrocolloid.

9. A method according to claim 1 wherein the substrate has a flat shape.

10. A method according to claim 1 wherein the substrate has a predetermined arcuate shape.

11. A method according to claim 1 wherein the substrate comprises a flexible material.

12. A method according to claim 1 wherein the substrate comprises a shape-retaining material.

13. A method according to claim 1 wherein the at least one location includes at least one of a toe, heel, ankle, trochanter, knee, sacrum, coccyx, buttocks, ischium, scapula, elbow and occiput.

14. A skin protective device for reducing pressure damage to skin of a person and consisting of:
    a substrate having an inner surface to be positioned adjacent the skin of the person, and an outer surface opposite the inner surface;
    an adhesive layer substantially covering the inner surface of said substrate for adhesively securing the substrate to the skin of the person;
    at least one fluid-filled cell on the outer surface of said substrate and positioned overlying said adhesive layer so that said substrate distributes pressure when applied to the skin of the person, the at least one fluid-filled cell retaining the fluid therein to cushion the skin of the person; and
    a removable layer on the adhesive layer to protect said adhesive layer prior to application to the skin of the person.

15. A skin protective device according to claim 14 wherein said at least one fluid-filled cell comprises a plurality of fluid-filled cells in a side-by-side relation.

16. A skin protective device according to claim 14 wherein the at least one fluid-filled cell defines an exposed outermost surface for the skin protective device.

17. A skin protective device according to claim 14 wherein said at least one fluid-filled cell is filled with at least one of a gas, liquid and gel.

18. A skin protective device according to claim 14 wherein said adhesive layer covers at least 75% of the inner surface of said substrate.

19. A skin protective device according to claim 14 wherein said substrate has a substantially uniform thickness throughout.

20. A skin protective device according to claim 14 wherein said substrate comprises a polymer; and wherein said adhesive layer comprises hydrocolloid.

21. A skin protective device according to claim 14 wherein said substrate has a flat shape.

22. A skin protective device according to claim 14 wherein said substrate has a predetermined arcuate shape.

23. A skin protective device according to claim 14 wherein said substrate comprises a flexible material.

24. A skin protective device according to claim 14 wherein said substrate comprises a shape-retaining material.

25. A skin protective device for reducing pressure damage to skin of a person and consisting of:
- a substrate and having an inner surface to be positioned adjacent the skin of the person, and an outer surface opposite the inner surface;
- an adhesive layer substantially covering the inner surface of said substrate for adhesively securing the substrate to the skin of the person;
- a plurality of fluid-filled cells on the outer surface of said substrate to define an exposed outermost surface for the skin protective device and positioned overlying said adhesive layer so that said substrate distributes pressure when applied to the skin of the person, the plurality of fluid-filled cells retaining the fluid therein to cushion the skin of the person; and
- a removable layer on the adhesive layer to protect said adhesive layer prior to application to the skin of the person.

26. A skin protective device according to claim 25 wherein said adhesive layer covers at least 75% of the inner surface of said substrate.

27. A skin protective device according to claim 25 wherein said substrate has a substantially uniform thickness throughout.

28. A skin protective device according to claim 25 wherein said substrate comprises a polymer; and wherein said adhesive layer comprises hydrocolloid.

29. A skin protective device according to claim 25 wherein said substrate comprises a flexible material.

30. A skin protective device according to claim 25 wherein said substrate comprises a shape-retaining material.

31. A skin protective device for reducing pressure damage to skin of a person and consisting of:
- an adhesive layer having an inner surface to be adhesively secured to the skin of the person, and an outer surface opposite the inner surface;
- at least one fluid-filled cell having an outer surface to cushion the skin of the person, and an inner surface opposite the outer surface, the outer surface of said adhesive layer substantially covering the inner surface of said at least one fluid-filled cell so that said adhesive layer distributes pressure when applied to the skin of the person, the at least one fluid-filled cell retaining the fluid therein to cushion the skin of the person; and
- a removable layer on the inner surface of said adhesive layer for protection thereof prior to application to the skin of the person.

32. A skin protective device according to claim 31 wherein said at least one fluid-filled cell comprises a plurality of fluid-filled cells in a side-by-side relation.

33. A skin protective device according to claim 31 wherein said at least one fluid-filled cell defines an exposed outermost surface for the skin protective device.

34. A skin protective device according to claim 31 wherein said at least one fluid-filled cell is filled with at least one of a gas, liquid and gel.

35. A skin protective device according to claim 31 wherein said adhesive layer covers at least 75% of the inner surface of said at least one fluid-filled cell.

36. A skin protective device according to claim 31 wherein said adhesive layer comprises hydrocolloid.

* * * * *